US006783294B2

(12) United States Patent
Duden et al.

(10) Patent No.: US 6,783,294 B2
(45) Date of Patent: Aug. 31, 2004

(54) SOLID CLEANSER HOLDER

(75) Inventors: Carol Duden, Lambertville, NJ (US); Linda McMeekin, Bound Brook, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 09/879,931

(22) Filed: Jun. 13, 2001

(65) Prior Publication Data
US 2002/0025215 A1 Feb. 28, 2002

Related U.S. Application Data

(63) Continuation-in-part of application No. 09/503,262, filed on Feb. 14, 2000.

(51) Int. Cl.[7] .................................................. A47K 7/02
(52) U.S. Cl. ........................................ 401/201; 401/196
(58) Field of Search ................................. 401/201, 196, 401/200; 428/35.2, 35.3, 35.5, 35.7, 35.9, 36.4, 36.9, 36.91, 36.92

(56) References Cited

U.S. PATENT DOCUMENTS

| | | |
|---|---|---|
| 1,351,311 A | 8/1920 | Virneberg |
| 2,102,858 A | 12/1937 | Schlumbohm |
| 2,209,914 A | 7/1940 | Gerber et al. |
| 2,607,940 A | 8/1952 | Miller |
| 2,961,677 A | 11/1960 | Zecchini |
| 2,980,941 A | 4/1961 | Miller |
| 3,054,148 A | 9/1962 | Zimmerli et al. ........... 264/154 |
| 3,167,805 A | 2/1965 | Zuppinger et al. |
| 3,306,292 A | 2/1967 | Spees |
| 3,324,500 A * | 6/1967 | Fuller et al. ................ 401/132 |
| 3,334,374 A | 8/1967 | Watkins, Jr. |
| 3,334,790 A | 8/1967 | Eaton |

(List continued on next page.)

FOREIGN PATENT DOCUMENTS

| | | |
|---|---|---|
| CA | 1158008 | 12/1983 |
| CA | 2007694 | 7/1990 |

(List continued on next page.)

OTHER PUBLICATIONS

European Search Report, dated Sep. 16, 2002 for EPO Appln. No. EP 02254106.
Rosato, Dominick V., *Rosato's Plastics Encyclopedia and Dictionary*, p. 119. Hanser Publishers, New York, 1993.
Decision from ROC Intellectual Property Office dated Mar. 8, 2004 for Taiwan APPL. No. 90103188.

Primary Examiner—David J. Walczak

(57) ABSTRACT

A solid cleanser holder comprising at least one textured film having texture variations including at least one aperture and a solid cleanser, wherein the at least one textured film surrounds the solid cleanser. The solid cleanser holders are not only gentle to the skin but also capable of reducing slip and creating superior lather. Methods of ameliorating the formation of mush on a solid cleanser are also disclosed. The method comprises enclosing a solid cleanser within a textured film having texture variations. Another embodiment relates to methods for making a solid cleanser holder. This method comprises enclosing a solid cleanser within a textured film such that the textured film surrounds the solid cleanser. Methods of cleansing and/or exfoliating the skin comprising the use of the solid cleansers described above are also disclosed.

49 Claims, 9 Drawing Sheets

U.S. PATENT DOCUMENTS

| | | |
|---|---|---|
| 3,362,776 A | 1/1968 | Knorr |
| 3,394,211 A | 7/1968 | MacDuff |
| 3,466,131 A | 9/1969 | Aroudi |
| 3,635,567 A | 1/1972 | Richardson, Jr. |
| 3,768,916 A | 10/1973 | Avery |
| 3,776,644 A | 12/1973 | Baker |
| 3,826,259 A | 7/1974 | Bailey |
| 3,860,349 A | 1/1975 | Scott |
| 3,929,135 A | 12/1975 | Thompson |
| 3,977,452 A | 8/1976 | Wright |
| 3,977,796 A | 8/1976 | Gillespie et al. |
| 3,989,393 A | 11/1976 | Frumkin et al. |
| 4,154,542 A | 5/1979 | Rasmason |
| 4,173,978 A | 11/1979 | Brown |
| 4,183,684 A | 1/1980 | Avery, Jr. |
| 4,188,304 A | 2/1980 | Clarke et al. .................. 252/93 |
| 4,189,802 A | 2/1980 | Lansbergen |
| 4,190,550 A | 2/1980 | Campbell |
| 4,228,834 A | 10/1980 | Desnick |
| 4,348,293 A | 9/1982 | Clarke et al. .................. 252/90 |
| 4,373,224 A | 2/1983 | Bandai et al. |
| 4,410,441 A | 10/1983 | Davies et al. .................. 206/0.5 |
| 4,436,780 A | 3/1984 | Hotchkiss et al. |
| 4,456,570 A | 6/1984 | Thomas et al. |
| 4,457,640 A | 7/1984 | Anderson |
| 4,457,643 A | 7/1984 | Caniglia |
| 4,469,463 A | 9/1984 | Van Overloop |
| 4,478,530 A | 10/1984 | Van Overloop |
| 4,480,939 A | 11/1984 | Upton |
| 4,515,703 A | 5/1985 | Haq |
| 4,525,091 A | 6/1985 | Van Overloop |
| 4,525,411 A | 6/1985 | Schmidt |
| 4,535,020 A | 8/1985 | Thomas et al. |
| 4,563,103 A | 1/1986 | Van Overloop et al. |
| 4,576,737 A | 3/1986 | Johnson |
| 4,582,625 A | 4/1986 | George |
| 4,473,611 A | 5/1986 | Haq |
| 4,603,069 A | 7/1986 | Haq et al. |
| 4,627,129 A | 12/1986 | Wittes |
| 4,629,643 A | 12/1986 | Curro et al. |
| 4,728,006 A | 3/1988 | Drobish et al. |
| 4,741,877 A | 5/1988 | Mullane, Jr. |
| 4,759,754 A | 7/1988 | Korpman |
| 4,772,444 A | 9/1988 | Curro et al. |
| 4,782,975 A | 11/1988 | Coy |
| 4,789,262 A | 12/1988 | Sanchez |
| 4,812,067 A | 3/1989 | Brown et al. |
| 4,818,421 A | 4/1989 | Boris et al. .................. 252/8.8 |
| 4,820,579 A | 4/1989 | Aszman |
| 4,839,216 A | 6/1989 | Curro et al. |
| 4,842,596 A | 6/1989 | Kielpikowski et al. |
| 4,904,524 A | 2/1990 | Yoh |
| 4,935,158 A * | 6/1990 | Aszman et al. ............. 401/201 |
| 4,953,250 A | 9/1990 | Brown .................... 15/104.94 |
| 4,969,225 A | 11/1990 | Schubert |
| 4,990,144 A | 2/1991 | Blott |
| 5,022,517 A * | 6/1991 | Benitez ...................... 401/201 |
| 5,024,799 A | 6/1991 | Harp et al. |
| 5,031,759 A | 7/1991 | Ogilvie |
| 5,053,270 A | 10/1991 | Mack ........................ 428/35.2 |
| 5,079,013 A | 1/1992 | Belanger |
| 5,090,832 A | 2/1992 | Rivera et al. |
| 5,098,755 A | 3/1992 | Tanquary et al. |
| 5,144,744 A | 9/1992 | Campagnoli |
| 5,207,725 A | 5/1993 | Pinkerton |
| 5,238,307 A | 8/1993 | Mooney et al. |
| 5,242,433 A | 9/1993 | Smith et al. |
| 5,254,109 A | 10/1993 | Smith et al. |
| 5,326,685 A | 7/1994 | Gaglio et al. |
| 5,366,125 A | 11/1994 | Procido |
| 5,409,640 A | 4/1995 | Giret et al. |
| 5,412,830 A | 5/1995 | Girardot et al. |
| 5,462,378 A | 10/1995 | Webb |
| 5,486,064 A | 1/1996 | Schulte |
| 5,492,646 A | 2/1996 | Langley et al. |
| 5,498,378 A | 3/1996 | Tsaur et al. |
| 5,525,397 A | 6/1996 | Shizuno et al. |
| 5,538,732 A | 7/1996 | Smith et al. |
| 5,558,874 A | 7/1996 | Haber et al. |
| 5,545,456 A | 8/1996 | Suida |
| 5,586,732 A | 12/1996 | Yamauchi et al. |
| 5,620,694 A | 4/1997 | Girardot |
| 5,632,420 A | 5/1997 | Lohrman et al. |
| 5,650,384 A | 7/1997 | Gordon et al. |
| 5,651,455 A | 7/1997 | Garcia |
| 5,680,969 A | 10/1997 | Gross |
| 5,681,574 A | 10/1997 | Haber et al. |
| 5,380,110 A | 1/1998 | Festa |
| 5,709,432 A | 1/1998 | Gryp ..................... 297/411.32 |
| 5,720,966 A | 2/1998 | Ostendorf |
| D392,466 S | 3/1998 | Kendall et al. |
| 5,727,278 A | 3/1998 | Per-Lee |
| 5,744,149 A | 4/1998 | Girardot |
| 5,784,747 A | 7/1998 | Girardot et al. |
| 5,795,644 A | 8/1998 | Delarosa |
| 5,802,539 A | 9/1998 | Gordon et al. |
| 5,802,655 A | 9/1998 | Denton |
| 5,804,539 A | 9/1998 | Gordon et al. |
| 5,839,842 A | 11/1998 | Wanat et al. |
| 5,857,794 A | 1/1999 | Chien |
| 5,895,163 A | 4/1999 | Chapman |
| 5,897,543 A | 4/1999 | Francis |
| 5,916,661 A | 6/1999 | Benson et al. |
| 5,980,931 A | 11/1999 | Fowler et al. |
| 6,012,411 A | 1/2000 | Hochbrueckner |
| 6,015,242 A | 1/2000 | Gillis |
| 6,042,288 A | 3/2000 | Rattinger et al. |
| 6,045,882 A | 4/2000 | Sandford |
| 6,048,407 A | 4/2000 | Schoch |
| 6,087,279 A | 7/2000 | Laun |
| 6,132,841 A | 10/2000 | Guthrie et al. |
| 6,209,165 B1 | 4/2001 | Frolova |
| 6,210,062 B1 | 4/2001 | Kokubo |
| 6,227,742 B1 | 5/2001 | Corn |
| 6,267,524 B1 | 7/2001 | Kroha |
| 6,318,922 B1 | 11/2001 | Briggs |
| 6,321,750 B1 | 11/2001 | Kelly |

FOREIGN PATENT DOCUMENTS

| | | |
|---|---|---|
| CA | 2007911 | 7/1990 |
| CA | 1283515 | 4/1991 |
| CA | 1323281 | 10/1993 |
| CA | 2295643 | 2/1999 |
| CA | 2260435 | 8/1999 |
| CA | 2010502 | 12/1999 |
| DE | 3441594 A | 5/1986 |
| EP | 0032793 B1 | 7/1981 |
| EP | 0170010 A | 2/1986 |
| EP | 0170821 A | 2/1986 |
| EP | 0252459 A1 | 1/1988 |
| EP | 0 340 993 A2 | 11/1989 |
| EP | 0388718 A2 | 9/1990 |
| EP | 0653635 A1 | 5/1995 |
| EP | 0728475 A2 | 8/1996 |
| EP | 0266929 B1 | 5/1998 |
| EP | 0873 711 A2 | 10/1998 |
| EP | 1 040 803 A1 | 10/2000 |
| EP | 1 125 541 A | 8/2001 |
| FR | 1364891 | 10/1964 |
| JP | 06/160486 A2 | 1/1966 |
| NZ | 206330 | 5/1986 |

| | | |
|---|---|---|
| NZ | 206331 | 5/1986 |
| WO | WO 89/07935 A1 | 9/1989 |
| WO | WO 94/12088 A1 | 6/1994 |
| WO | WO 95/00116 A2 | 1/1995 |
| WO | WO 95/26670 A1 | 10/1995 |
| WO | WO 96/04836 A1 | 2/1996 |
| WO | WO 96/10429 A2 | 4/1996 |
| WO | WO 96/11673 A1 | 4/1996 |
| WO | WO 96/23439 A1 | 8/1996 |
| WO | WO 97/07780 A1 | 3/1997 |
| WO | WO 97/07781 A1 | 3/1997 |
| WO | WO 97/24053 A1 | 7/1997 |
| WO | WO 97/35564 A1 | 10/1997 |
| WO | WO 97/38843 A1 | 10/1997 |
| WO | WO 98/18441 A1 | 5/1998 |
| WO | WO 98/18442 A1 | 5/1998 |
| WO | WO 98/18444 A1 | 5/1998 |
| WO | WO 98/18445 A1 | 5/1998 |
| WO | WO 98/18446 A1 | 5/1998 |
| WO | WO 98/28399 A1 | 7/1998 |
| WO | WO 98/50012 A1 | 11/1998 |
| WO | WO 98/55109 A1 | 12/1998 |
| WO | WO 99/09873 A1 | 3/1999 |
| WO | WO 00/75035 A1 | 12/2000 |
| WO | WO 01/85002 A1 | 11/2001 |

* cited by examiner

SOLID CLEANSER HOLDER

CROSS-REFERENCE TO RELATED APPLICATION

This application is a continuation-in-part application of U.S. application Ser. No. 09/503,262 filed on Feb. 14, 2000, which is incorporated herein by reference in its entirety.

FIELD OF THE INVENTION

This invention is generally related to the field of cleansing and/or scrubbing solid cleanser holders, and methods for their use and manufacture. More particularly, this invention is related to soft, textured cleansing and/or scrubbing solid cleanser holders for personal hygiene, and methods for their use.

BACKGROUND OF THE INVENTION

Although solid cleansers are highly popular personal cleansers they are not without problems. One problem associated with using solid cleansers, such as soap bars, is that the bar becomes very slippery when wet and easily dropped. Another problem associated with solid cleansers is that it eventually becomes so small and difficult to handle that many consumers discard the solid cleanser once it becomes small resulting in waste. Other problems associated with the use of bar soap include the formation of mush. Mush is wet soap that has softened, typically after sitting in water for a period of time. Mush typically forms on the bottom of the solid cleanser and is quite undesirable. Another problem associated with solid cleansers is poor lathering ability.

Cleansing implements have been developed to be utilized with bar soaps or liquid personal washing cleansers. One known cleansing implement includes the sponge, see e.g., U.S. Pat. No. 4,627,129 (reticulated polyurethane foam sponge). However, such sponges tend to retain moisture and cleansing materials and thus promote mold and microbial growth.

Another known cleansing implement includes the polymer mesh puffs, see e.g., U.S. Pat. Nos. 5,727,278, 5,144,744, and 5,784,747. However, such puffs tend to be rather abrasive and rough on the skin.

Yet another known cleansing implement is a "closed sandwich" structure comprised of two substrate layers bonded together to form a plurality of compartments for soap and the like as disclosed in U.S. Pat. No. 4,515,703. However, because these solid cleanser holders have a relatively low open area, they are capable of producing only a relatively small amount of lather and also tend to retain moisture.

It would be desirable to have a solid cleanser holder that would not only be gentle to the skin but would also not retain moisture, would be easier to hold and produce superior lather.

SUMMARY OF THE INVENTION

In accordance with this invention, there is provided a solid cleanser holder comprising:
  a. at least one textured film having texture variations including at least one aperture; and
  b. a solid cleanser, wherein the at least one textured film surrounds the solid cleanser.

The solid cleanser holders of this invention are not only gentle to the skin but also capable of reducing slip and creating superior lather. The invention also relates to methods of ameliorating the formation of mush on a solid cleanser. The method comprises enclosing a solid cleanser within a textured film having texture variations. Another embodiment of the invention relates to methods for making a solid cleanser holder. This method comprises enclosing a solid cleanser within a textured film such that the textured film surrounds the solid cleanser. The invention also relates to methods of cleansing and/or exfoliating the skin comprising the use of the devices described above.

DESCRIPTION OF THE DRAWINGS

The invention will be more fully understood and further advantages will become apparent when reference is made to the following detailed description of the invention and the accompanying drawing in which.

DETAILED DESCRIPTION OF PREFERRED EMBODIMENTS

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

As discussed above, the invention relates to a solid cleanser holder comprising:

a. at least one textured film having texture variations including at least one aperture; and
b. a solid cleanser, wherein the at least one textured film surrounds the solid cleanser.

In a preferred embodiment, the at least one textured film is substantially permanently sealed around the solid cleanser.

Figure 7:
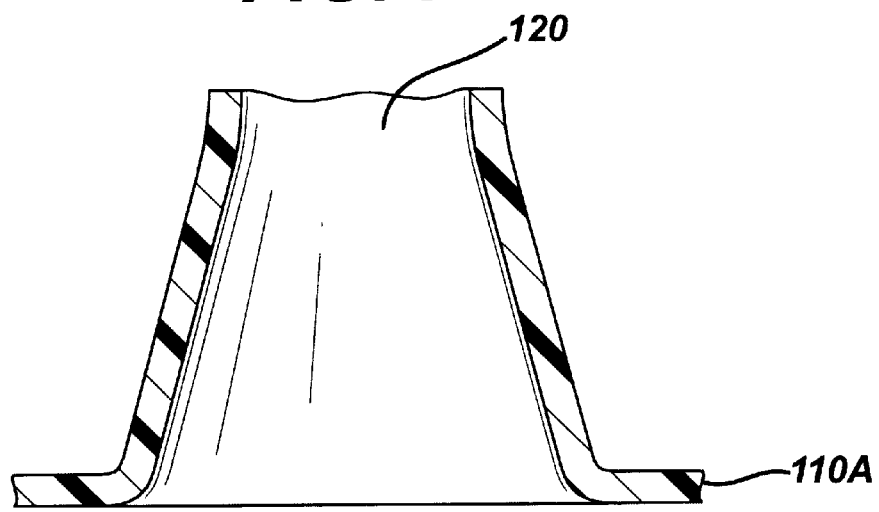
FIG. 7 is a representation of an enlarged cross sectional view of the protuberance as referenced by encircled area of FIG. 6.
Figure 8:
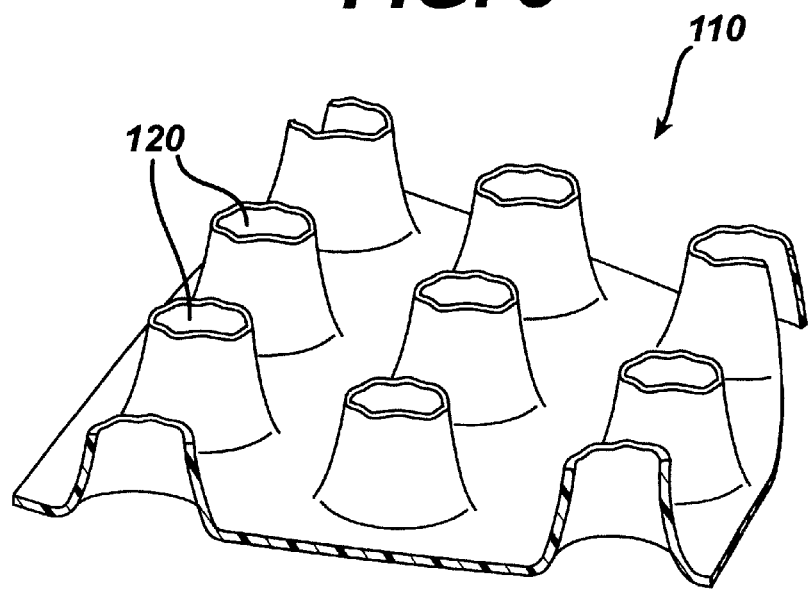
FIG. 8 is a representation of a perspective view of a portion of one layer of apertured film wherein the apertures are protuberances.

As used herein, the term, "texture variations," shall mean apertures (holes, slits or protuberances), debossments, or embossments in the film. By "textured film" it is meant any film with at least one texture variation. As used herein, "substantially permanently" means a period of time at least as long as the film of the solid cleanser holder is suitable for cleansing uses. By "protuberance" it is meant a texture variation in which there is a first hole in the film and a second hole in a different plane which is separated from but connected to the first hole by a continuous wall of film. See for example FIGS. 7 and 8. By "gathered," it is meant to fold, pleat, smock, or any other known technique for pulling the film together into the desired shape. See for example, FIG. 2. The term, "nonwoven web," shall mean a web of material that is formed without the aid of a knitting or a textile weaving process.

The Textured Film

Examples of suitable textured films useful in the present invention include, but are not limited to, those comprised of polyolefins, cellulosics, polyurethanes, polyamides, polyesters, metallocene polyethylenes and blends and copolymers thereof. Preferably, the textured film is comprised of polyethylenes, polypropylenes, polyvinyl acetates, polyacrylates, polyvinyl chloride, polyvinylidine chloride, polyvinyl alcohol and blends and copolymers thereof, polyolefins, such as described, for example, by U.S. Pat. Nos. 4,456,570 and 4,535,020. Examples of suitable commercial perforated films include those available from Tredegar Film Products, Inc. under the tradename, VISPORE® from Polymer Group, Inc. under the tradename, RETICULON®, or from Guial Inc. under the tradename, VEOLE, with the VISPORE® film being preferred.

The texture variations of the textured films may be created in the films via known processes, see, e.g., U.S. Pat. Nos. 4,741,877; 3,929,135 and 3,394,211; 3,929,135; 3,394,211; 4,629,643 and 4,839,216 and European Patent Application No. 1,040,803.

Figure 6:
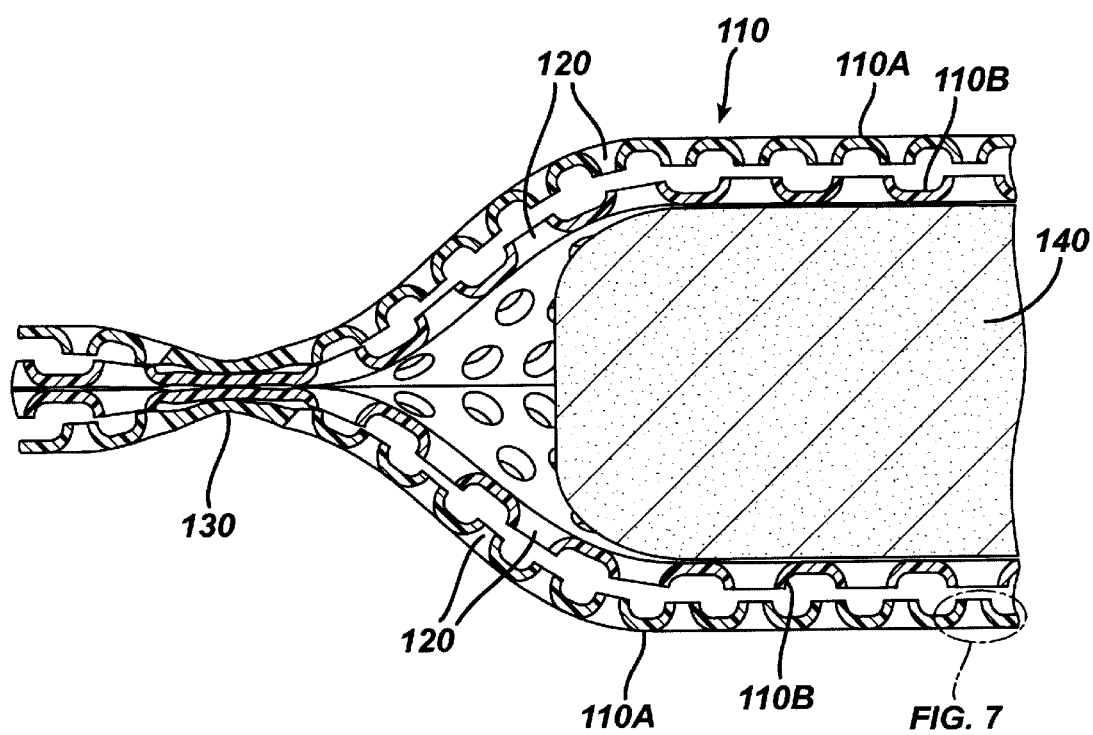
FIG. 6 is a representation of an enlarged cross sectional view of the solid cleanser holder as taken along line 6—6 of FIG. 1 depicting two different textured films, with protuberances facing toward one another that are wrapped around the solid cleanser.
Figure 10:
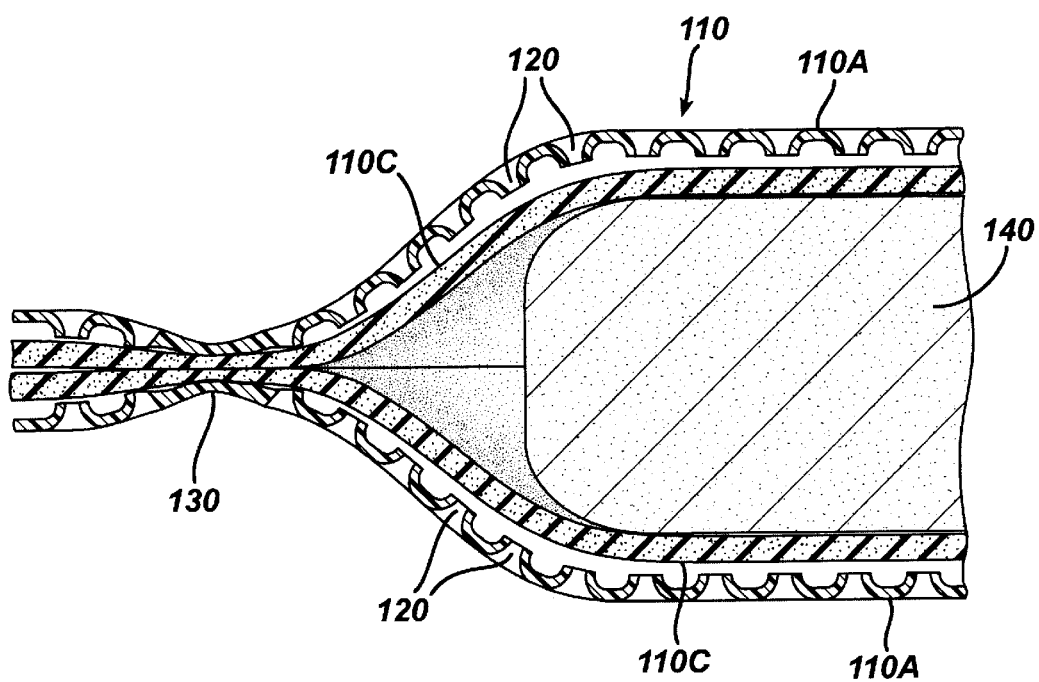
FIG. 10 is a representation of a cross sectional view similar to FIG. 6 depicting a solid cleaner holder comprising an inner substrate substantially covered by a textured film.

Generally speaking, the resulting textured film possesses a rough side and an opposing smooth side. By "smooth" side, it is meant the side from which the texture variations originate. By "rough" side it is meant the side opposite the smooth side. Where the texture variations are protuberances, the protuberances are generally cone-shaped. It would be obvious to one skilled in the art that where the texture variations are embossments or debossments, they could be in a variety of shapes. The protuberances can be facing inward or outward. FIG. 10 depicts protuberances (120) facing inward toward the solid cleanser (140). For example, in uses where exfoliation is of importance, it is preferable to have the protuberances facing outward. FIG. 6 depicts protuberances (120) facing outward away from the solid cleanser (140).

The type and dimensions of texture variations in the textured film may vary depending upon, for example, the type of solid cleanser, the rate of release of solid cleanser, the ease of rinsability, the size of bubbles, and the volume of lather desired. Embossment texture variations alone generally are not sufficient to provide improved lathering. Accordingly, the textured films suitable for use in the solid cleanser holders of the present invention include at least one aperture. Generally, the textured film comprises multiple apertures in an amount ranging from about 0.1 apertures/$cm^2$ to about 300 apertures/$cm^2$, more preferably, from about 1.3 apertures/$cm^2$ to about 30 apertures/$cm^2$, most preferably, from about 1.5 apertures/$cm^2$ to about 15 apertures/$cm^2$. In a preferred embodiment, the apertures have a depth of greater than 0 mm to about 3 mm.

The size of the apertures, measured as the average diameter of the apertures across the smooth side of the textured film, ranges in size from about 0.01 cm to about 0.6 cm, and preferably from about 0.05 cm to about 0.4 cm, and more preferably from about 0.1 cm to about 0.35 cm. In embodiments where it is desirable to slowly deplete the solid cleanser, it is preferable to use apertures having a relatively smaller average diameter, i.e. less than about 0.1 cm.

In a preferred embodiment, the texture variations comprise a combination of apertures and at least one additional texture variation selected from the group consisting of embossments, debossments, and mixtures thereof. Where debossments or embossments are present, they are generally present in an amount up to about 7000 debossments or embossments/$cm^2$.

One example of suitable embossment texture variations is disclosed in U.S. Pat. Nos. 4,629,643 and 4,839,216 and European Patent Application No. 1,040,803. The depth of the embossment texture variations, as measured from the smooth side of the apertured film to the bottom of the embossment, may range from about greater than about 0 cm to about 0.4 cm, and preferably between about 0.005 cm to about 0.3 cm. In embodiments wherein rinseability is of concern, it is preferable to use either an apertured film or an embossed film having a depth of embossment of greater than about 0.05 cm.

The texture variations may be of any shape that can perforated or embossed into the film. Although the shape of the texture variation will generally depend upon, for example, aesthetics desired. The texture variations can be in the approximate shape of a circle, polygon, honeycomb, oval, heart, pear, square, triangle, stellate, rectangle, star, or combinations thereof.

The textured films suitable for use in the present invention preferably are apertured films having an open area of no more than about 45%, and preferably greater than about 15% to about 35%, based upon the total area of the apertured film. Typically, the open area of a film is expressed in terms of "% open area," which is equal to 100×area fraction. "Area fraction" as used herein, may be calculated as the sum of the areas of the holes (in a two-dimensional film) or sum of the areas of the minimum opening of the protuberances (in a three dimensional film) divided by the total area examined.

One type of textured film suitable for use in the solid cleanser holders of the present invention further possesses general mechanical properties as shown below in Table A:

TABLE A

Mechanical Properties

| Type of Material | Force to stretch to 20% elongation* N/m (lb$_f$/in) | Force to stretch to 50% elongation* N/m (lb$_f$/in) | Direction of Stretch | Tensile Strength* N/cm (lb$_f$/in) | Elasticity# |
|---|---|---|---|---|---|
| Textured Film suitable for use in present invention | 35–263 (0.2 to 1.5) and preferably 35–175 (0.2 to 1.0) | 88–350 (0.5 to 2.0) and preferably 88–263 (0.5 to 1.5) | Machine | >263 (>1.5) | About 60%- less than about 100%, and preferably from about 80% to less than about 100% |

*Using ASTM D-882
Measured by the % recovery from a 50% elongation using an Instron testing machine The textured films suitable for use in the solid cleanser holders of the present invention are preferably three-dimensional. We have found that the three dimensional solid cleanser holders made from textured films were not only very soft and gentle to the skin, but were capable of producing a large quantity of lather.

In one embodiment, the material used to surround the solid cleanser may be comprised of a perforated calendered nonwoven material. Nonwovens are well known in the art. Any nonwoven material may be utilized in the present invention. The nonwoven material is calendered to increase the density of the material, then apertured and/or embossed through processes known in the art, such as needle punching and the like. The nonwoven materials may contain the same size apertures and embossments as described above. The number of apertures and embossments per unit area is as described for the materials above.

In another embodiment as illustrated by FIG. 10, the material surrounding the solid cleanser may further comprise an inner substrate (110C) that is substantially covered by the textured film. The inner substrate may be comprised of an open-celled mesh sheet, porous foam sheet, reticulated foam sheet, natural fiber sheet, polymeric fiber (filament, staple, spunbond, or meltblown) sheets, and combinations thereof.

The textured film utilized in the present invention may have materials, such as film modifiers, added to it to improve the performance of the solid cleanser holder. The film modifier may be impregnated into and/or deposited onto the textured film. Any film modifier known in the art to enhance the physical and/or aesthetic properties of the film may be added. Examples of suitable film modifiers include surfactants, antimicrobial agents, colorants, fragrances, fillers, silica, pumice, mica, and mixtures thereof.

A surfactant may be added in an amount effective to improve wetting. Any surfactant including, but not limited to, nonionics, anionics, cationics, amphoterics, betaines, and combinations thereof may be utilized. The surfactants may be incorporated into the substrate during the process of making the film (i.e., be included in the polymerization process for making polymers that are used to make apertured films). Alternatively, the surfactant may be impregnated, deposited and/or coated onto or into the apertured film by means known in the art.

Figure 9:
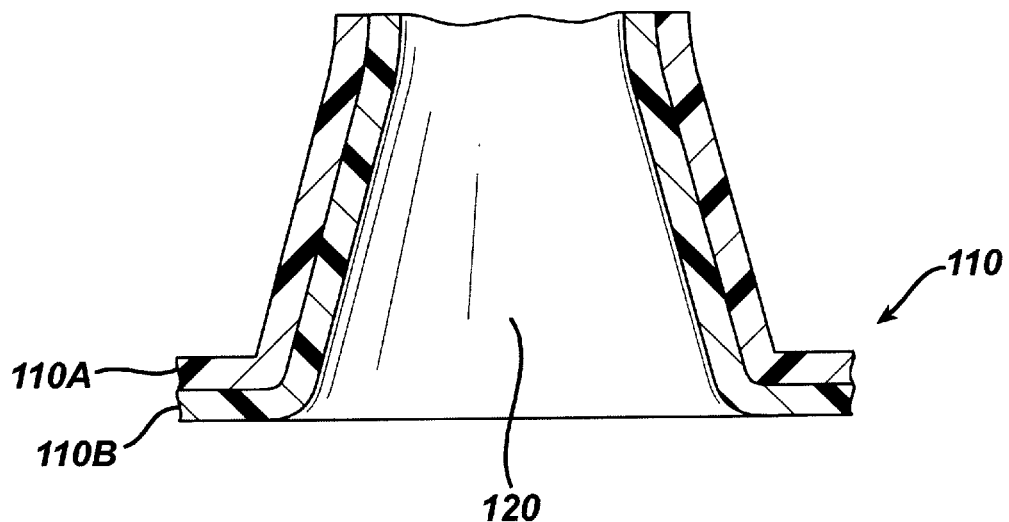
FIG. 9 is a representation of a cross sectional view of a protuberance in a textured film which is a coextruded layer comprising at least two layers.

The textured film used in the solid cleanser holder according to the invention may be comprised of a coextruded film comprising at least two layers made by coextrusion. Coextrusion provides composite multiple layers—usually using one or more extruders with melts going through one die— that are bonded together. See, for example, Rosato's Plastics Encyclopedia and Dictionary, p. 119, 1993. FIG. 9 depicts a cross sectional view of a protuberance in a textured film which is a coextruded layer comprising at least two layers (110A and 110B). In an alternative embodiment, the textured film comprises at least 2-plies of film sheets which can be separate substrates sealed together along the periphery or one substrate that is folded upon itself and then sealed. FIG. 6 depicts a textured film comprising one substrate folded upon itself and then sealed to form 2-plies of film sheets (110A and 110B) comprising protuberances (120) facing toward one another.

The Solid Cleanser Holder

Figure 1:
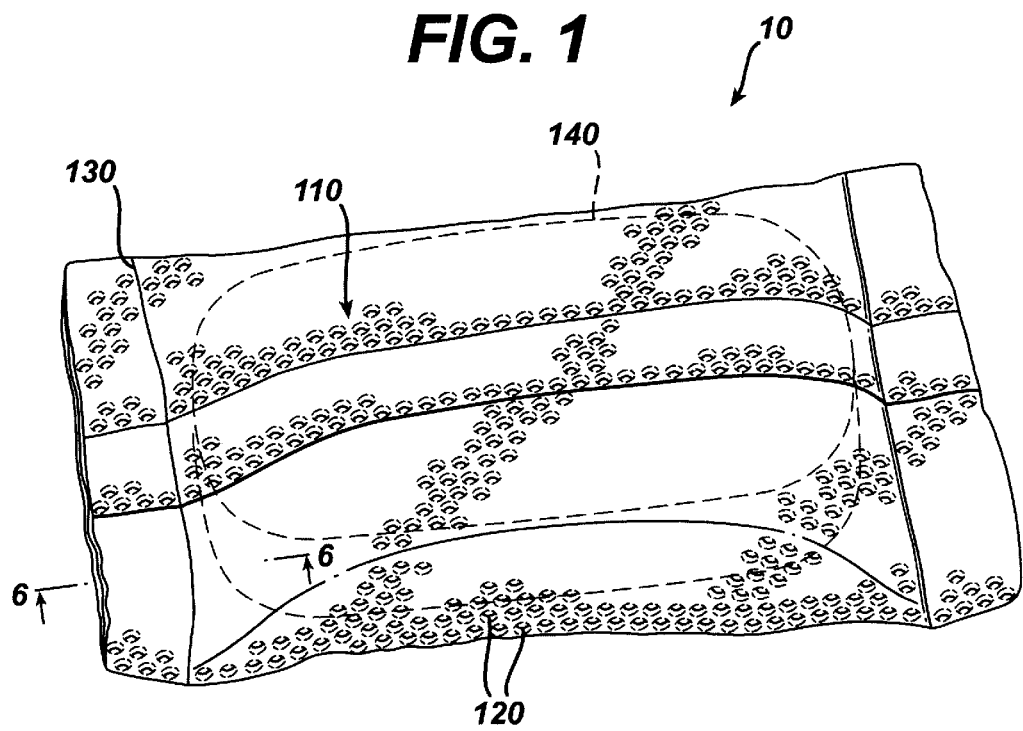
FIG. 1 is a representation of one embodiment of the solid cleanser holder according to the invention wherein the solid cleanser holder (10) comprises at least one textured film (110), having textured variations including at least one aperture (120) and a solid cleanser (140), wherein the at least one textured film surrounds the solid cleanser and is sealed (130) on three sides to substantially permanently surround the solid cleanser.

The solid cleanser holders according to the invention may be prepared by enclosing a solid cleanser within a textured film such that the textured film surrounds the solid cleanser. In a preferred embodiment, the textured film is substantially permanently sealed around the solid cleanser holder. Preferably, the solid cleanser holder comprises at least two textured films that are wrapped around the solid cleanser and are substantially permanently sealed together. In a particularly preferred embodiment as shown by FIGS. 1 and 6, the solid cleanser holder (10) comprises two different textured films (110A and 110B), with protuberances (120) facing toward one another that are wrapped around the solid cleanser and sealed (130) on three sides to substantially permanently surround the solid cleanser (140). The textured film in the solid cleanser holder may be secured together via any of the securing techniques known in the art, such as, for example, heat sealing, heat shrinking, ultrasonic sealing, adhesive sealing, stitch sealing, and pressure sealing, with heat sealing being preferred.

In an alternative preferred embodiment, each surface of the solid cleanser holder may be comprised of at least one ply of textured film, wherein the texture variation of one surface is different from the texture variation of the other surface. For example, in the latter embodiment, the one surface may be comprised of a textured film with the protuberances facing outward and the other surface may be comprised of same but with the protuberances facing inward toward the solid cleanser. Alternatively, the outer ply of the textured film of one surface may have smaller textured variations than the outer ply of the textured film of the other surface.

The solid cleanser holder and the solid cleanser may be any shape suitable for a solid cleanser, such as, but not limited to, round, square, rectangular, oval, star shaped, polygon, in the shape of an animal, a hand, a mitt and the like.

Figure 2:
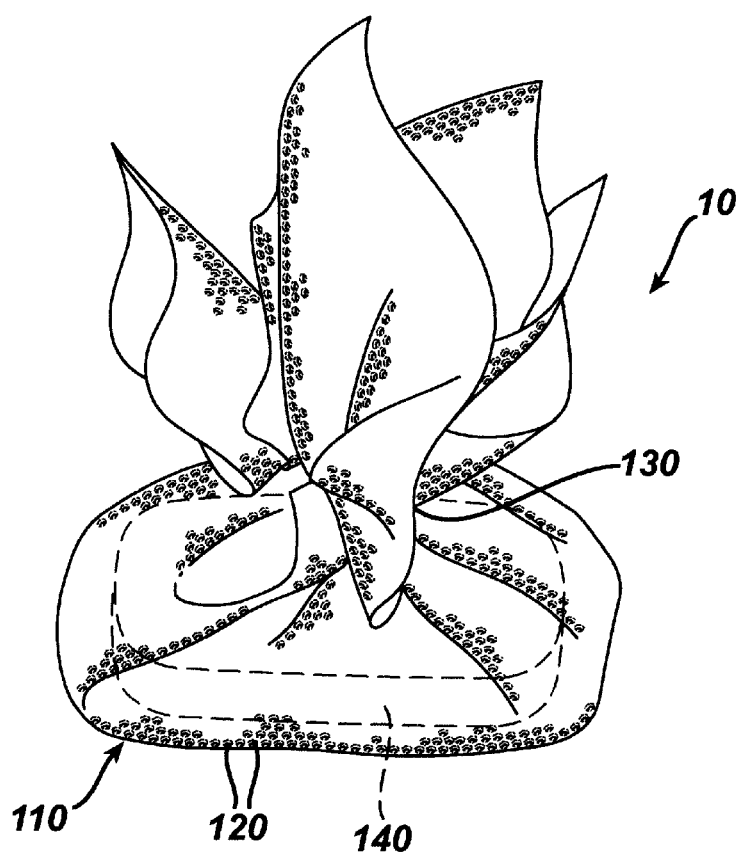
FIG. 2 is a representation of one embodiment of the solid cleanser holder (10) according to the invention wherein the textured film (110) continuously surrounds the solid cleanser (140) and is gathered and secured with a securing means (130) for substantially permanently holding the gathered textured film together.
Figure 3:
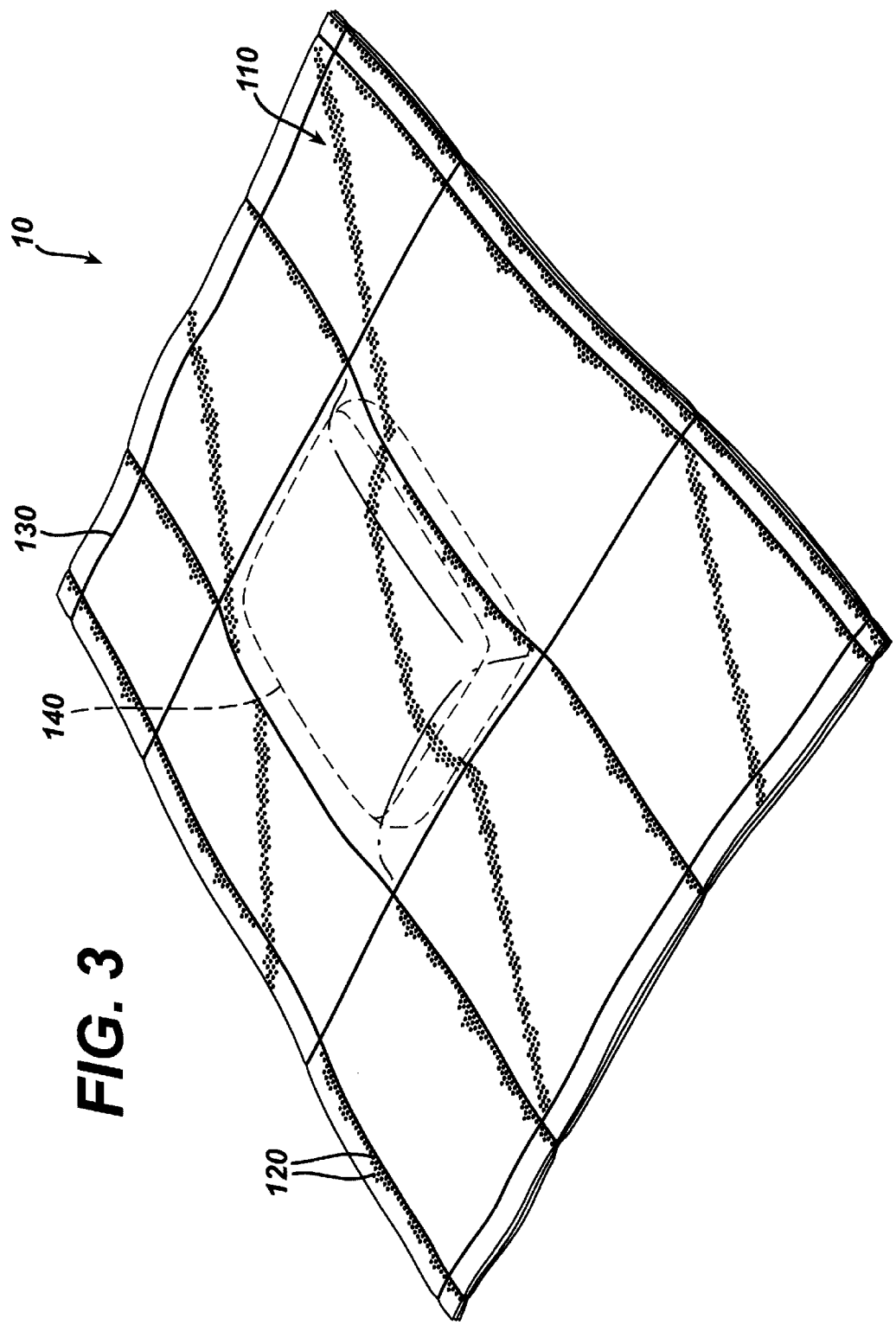
FIG. 3 is a representation of one embodiment of the solid cleanser holder (10) according to the invention wherein the textured film (110) continuously surrounds the solid cleanser (140) and is in the form of a layered sheet sealed (130) on four sides.

The solid cleanser holder may be configured in a variety of ways. For example, as shown in FIG. 2, the textured film (110) may continuously surround the solid cleanser (140), wherein said textured film is gathered and secured with a securing means (130) for substantially permanently holding the gathered textured film together. In another embodiment, the textured film continuously surrounds the solid cleanser and is sealed on one or more sides. For example, the textured film (110) may continuously surround the solid cleanser (140), wherein said textured film is in the form of layered sheets and sealed (130) on four sides as shown in FIG. 3.

Figure 4:
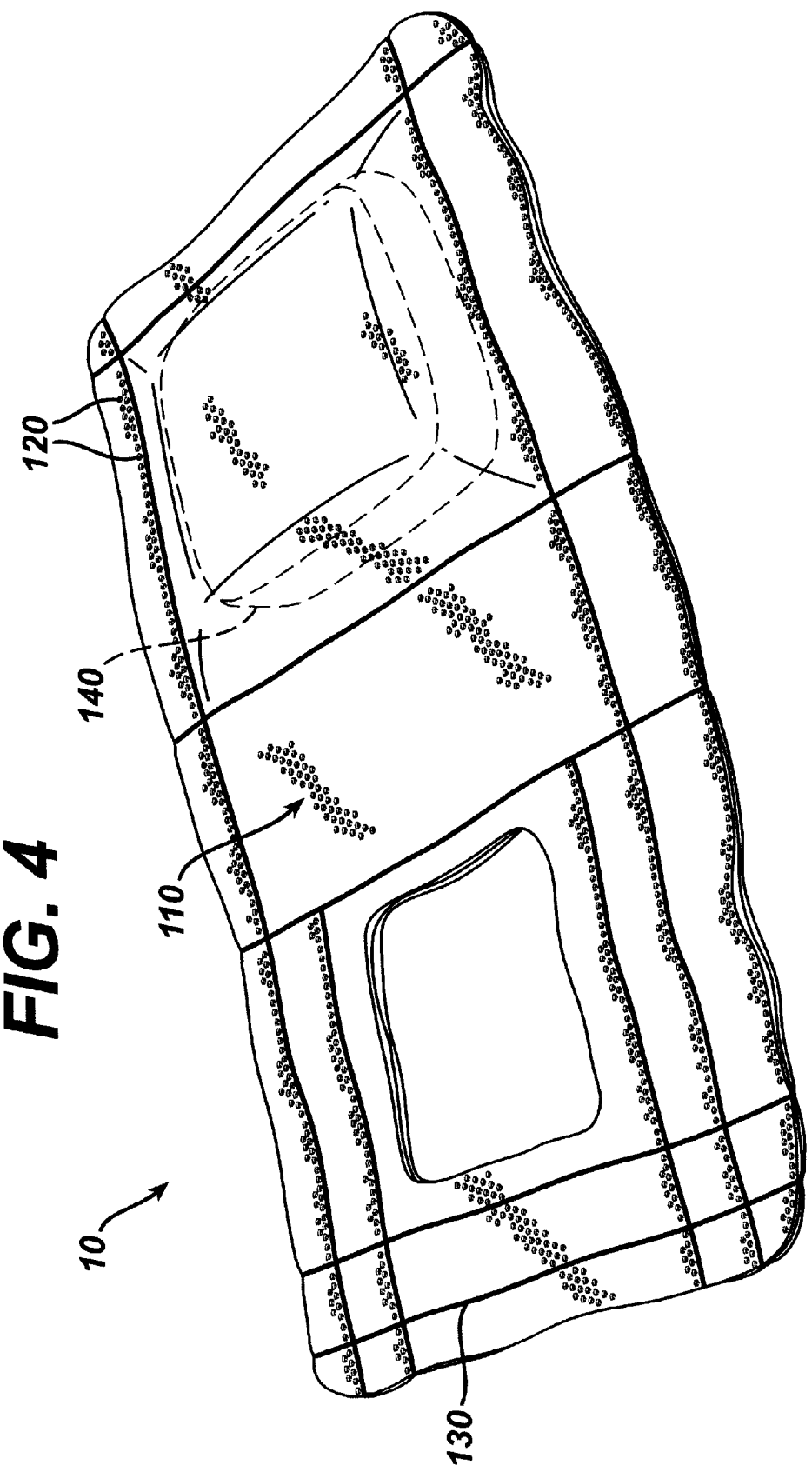
FIG. 4 is a representation of one embodiment of the solid cleanser holder according to the invention wherein the solid cleanser holder further comprises a holding and/or hanging means made from a continuous piece of the textured film.
Figure 5:
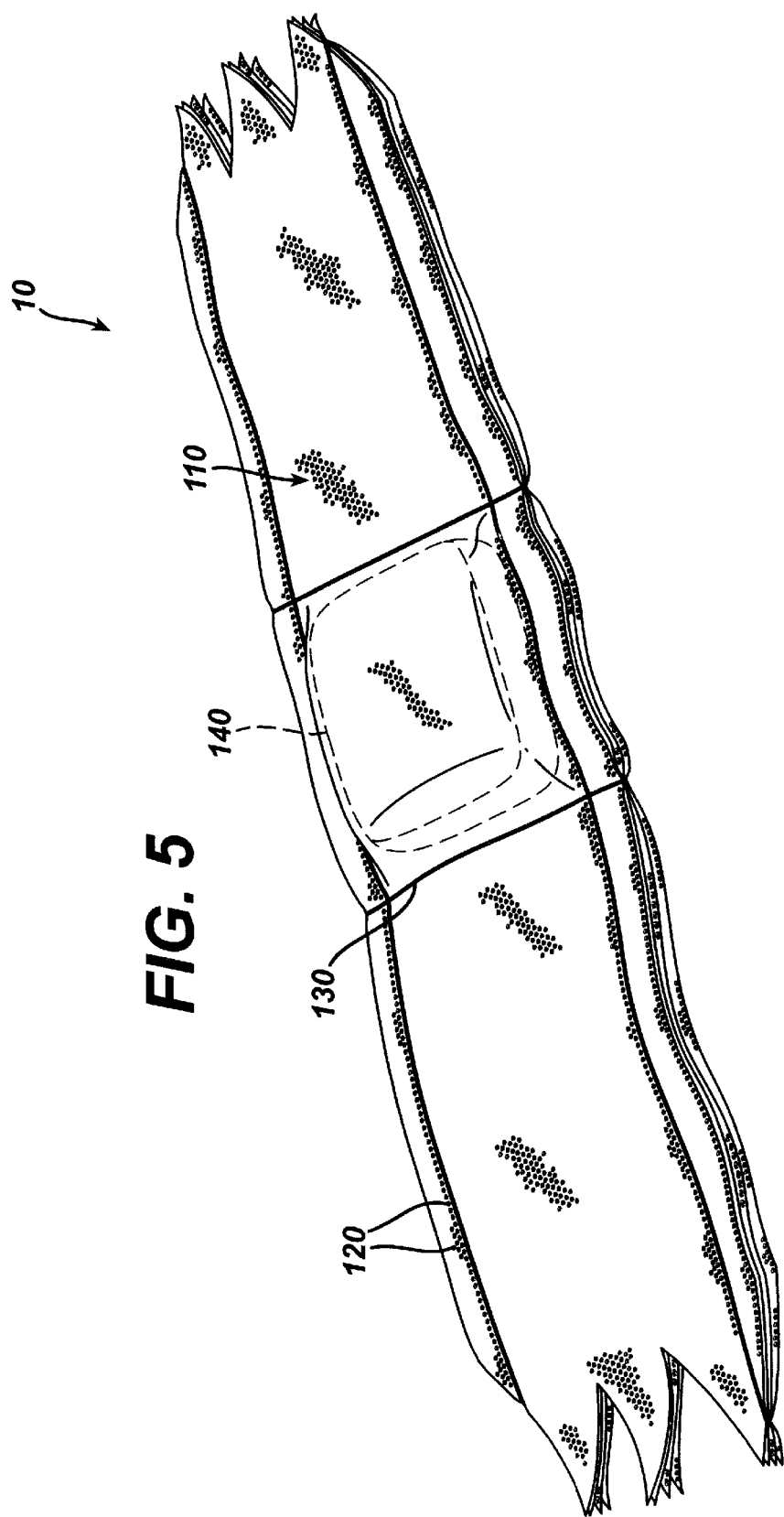
FIG. 5 is a representation of one embodiment of the solid cleanser holder according to the invention wherein the solid cleanser holder further comprises a holding and/or hanging means made from an attached piece of textured film.

In another embodiment, the solid cleanser holder may further comprise a holding and/or hanging means. Example of suitable holding and/or hanging means include hooks, loops, straps or strings. Such solid cleanser holding and/or hanging means may be made from a continuous piece of the textured film as shown in FIG. 4. Alternatively, the holding and/or hanging means may be an extended piece attached to the solid cleanser holder as shown in FIG. 5.

The Solid Cleanser

The type of solid cleanser used in the solid cleanser holder according to the invention is not critical. Generally, a solid cleanser is any cleanser that is not in liquid form. Examples, include but are not limited to, a bar, flake, pellet, chip, spray-dried powder, noodle, semi-solid, gel, moldable paste and combinations thereof. The solid cleanser may be comprised of soap and/or synthetic surfactants. For example, the solid cleanser may include soaps derived from hydrocarbon chain lengths of from approximately 10 to 22 (including carboxyl carbon) and are preferably saturated. It is preferred that the soap be the sodium salts, but other soluble soap can be used. Potassium, ammonium, triethanolammonium and mixtures thereof are deemed acceptable. The soaps are preferably prepared by in situ saponification or ion exchange with a halide salt of the corresponding fatty acids, but they may also be introduced as preformed soaps. Either some or all of the soap is preferably precomplexed with cationic polymer, or polymers, when polymer is used.

Suitable synthetic surfactants include those known in the art, preferably, those known in the art for personal cleansing. Examples of suitable surfactants include the isethionates, sarcosinates, and glyceryl ether sulfonates which may be pure chain length variants or those derived from commercial oils such as coconut oil, Here the lauryl chain length should preferably account for at least 20% to as much as 100% of the weight of the given surfactant.

Numerous examples of other surfactants in general are included in the list appropriate for this invention. These include limited amounts of anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines and mixtures thereof. Included in the surfactants are the alkyl ether sulfates with 1 to 12 ethoxy groups, especially ammonium and sodium lauryl ether sulfates. Alkyl chains for these other surfactants are $C_8-C_{22}$, preferably $C_{10}-C_{18}$. Alkyl glucosides and methyl glucoside esters are preferred mild nonionics, which may be mixed with other mild anionic or amphoteric surfactants in the compositions of this invention.

The solid cleansers of this invention can have from 0–10 percent high lathering, non-mild surfactants including linear alkyl benzene sulfonates and shorter chain or traditional (coconut) alkyl sulfates. The synthetic detergent bar may contain a mixture of sodium topped distilled $C_{12}-C_{18}$ cocoyl isethionate and sodium linear alkylbenzene sulfonate.

Binders may be incorporated into the solid cleanser. The binder may be a liquid water-soluble aliphatic polyol or polyethylene glycol or polypropylene glycol. The polyol may be saturated or contain ethylenic linkages. If desired, the compound may have an alcohol group attached to each carbon atom in the chain. Among the compounds include ethylene glycol, propylene glycol and glycerin.

The solid cleaner bar in this invention may contain many additives to improve the function or aesthetics of the bar. Included are fast hydrating cationic polymer, perfumes, vegetable oils, mineral oils, alcohols, hydrotropes, colorant, fillers (such as talc, clay, calcium carbonate), preservatives, antibacterial agents, salts (both organic and inorganic).

The solid cleanser may also contain components to control odor, i.e. zeolites, cetyl peridium chloride, zinc chloride, EDTA, BHT and the like. Further, the solid cleanser may contain the "active materials" described in copending application Ser. No. 09/503,262.

The Benefits

The solid cleanser holders of this invention are capable of reducing slip, e.g., the ability of the bar to fall, slide or glide from the hands during the cleansing process. As shown by Example 3, the solid cleanser holders have significantly reduced slip properties when compared to conventional solid cleansers.

The solid cleanser holders of this invention are capable of improving lather. Accordingly, in one embodiment, the invention relates to a method of improving the lathering abilities of a solid cleanser comprised of enclosing a solid cleanser within a textured film such that the textured film surrounds the solid cleanser, wherein the textured film comprises texture variations including at least one aperture.

One advantage of the solid cleanser holder according to the invention is that the solid cleanser holder is capable of drying quickly. A further advantage of the solid cleanser holder of the invention is that it is longer lasting than a standard solid cleanser because the solid cleanser holder provides a barrier between the solid cleanser and the skin, thereby reducing the wear rate of the solid cleanser.

Due to their quick drying nature, solid cleanser holders according to the invention are capable of reducing the mush associated with standard solid cleanser. Mush is wet cleanser that has softened, typically after sitting in water for a period of time. Mush typically forms on the bottom of the solid cleanser and is quite undesirable.

The solid cleanser holder according to the invention can be particularly useful for personal cleansing bars. As cleansing bars are used up, they tend to become thin and break, leaving small pieces of cleanser that are wasted. The solid cleanser holders according to the invention solve this problem, as any solid cleanser that breaks off from the main bar is retained within the holder, and ultimately used.

In another embodiment, the invention relates to a method of exfoliating the skin comprised of wetting the solid cleanser holder with water; applying agitation to the wet solid cleanser holder, wherein the amount of water and agitation is sufficient to create a lather on the solid cleanser holder, applying said lathering solid cleanser holder to the skin, and rinsing with water. The extent of the exfoliation will depend upon the size and dimensions of the texture variations and the film composition.

The solid cleanser holders according to the invention may be used in the same manner in which conventional solid cleansers are used. In one embodiment, the solid cleanser holders may be used in a method of cleansing the skin. The method comprising wetting the solid cleanser holder with water; applying agitation to the wet solid cleanser holder, wherein the amount of water and agitation is sufficient to create a lather on the solid cleanser holder, applying said lathering solid cleanser holder to the skin, and rinsing with water. Alternatively, the solid cleanser holders according to the invention may be used to clean any surface, for example, walls, countertops, cars, appliances, animals, toys, shoes, etc.

The solid cleanser holders of this invention are capable of reducing slip, e.g., the ability of the bar to fall, slide or glide from the hands during the cleansing process. As shown by Example 3, the solid cleanser holders have significantly reduced slip properties when compared to conventional solid cleansers. Preferably, the solid cleanser holder has an angle to slip of at least 5°.

EXAMPLES

Manufacture and Use of the Solid Cleanser Holder

A solid cleanser holder was prepared by cutting two 10 cm×6 cm pieces of Tredegar X-27340 lot #10082401 apertured film. One piece of film was overlayed on another and the top and bottom edges of the films were brought together and heat sealed. The left side edges of the films were then brought together and heat sealed. A bar of Johnson's® Baby Soap, commercially available from Johnson & Johnson India, was placed inside the holder and the right side edges were brought together and heat sealed. Approximately 20 solid cleanser holders were prepared following the same process with the same materials.

A series of experiments was performed to determine if this solid cleanser holder improves the performance of bar soap. In particular, weight loss after repeated hand washing, foam production after repeated hand washing and a laboratory measurement of slip were analyzed.

Example 1

Soap Bar Weight Loss

The weights of the soap bars were recorded to determine the amount of product lost after each use. Each soap bar was weighed prior to first use. The film was also weighed before it was put on the soap bar. Also, the total weight of the soap bar and the film was recorded before use. Using tepid water, each soap bar was initially wet and then turned 20 times by hand. The soap bar was then placed on a plastic film to dry. The foam that had formed was scraped off the hands with a tongue depressor and placed in a tared weigh dish. The foam weight was then recorded. This process was repeated for 10 soap bars with film and 10 soap bars without film.

All soap bars were left to dry overnight. The following morning, the soap bars were turned over and left to continue drying. In the afternoon, the soap bars were weighed and their weights were recorded. The hand-washing process was then repeated for each soap bar. Soap bar weights were measured during 16 hand-wash cycles; foam weights were measured for 10 cycles.

Analysis Variable Soap Bar Weight at Baseline

|  | Mean | N | Std Dev | Std Error | Minimum | Maximum |
|---|---|---|---|---|---|---|
| No Film | 49.48 | 10 | 0.20 | 0.06 | 49.24 | 49.90 |
| Film | 50.75 | 10 | 0.47 | 0.15 | 50.07 | 51.44 |

At the start of the study, before testing, due to the weight of the film, the 10 soap bars with film were slightly but consistently heavier than the 10 bars without film (P<0.001).

Table C shows summary statistics for soap bar weights in grams during 16 hand wash cycles. The mean cumulative weight loss in grams during 16 hand wash cycles is listed in Table D.

TABLE C

| | Apertured Film | | | |
|---|---|---|---|---|
| | No | | Yes | |
| Cycle | Mean | Std | Mean | Std |
| 0 | 49.5 | 0.20 | 50.7 | 0.47 |
| 1 | 49.1 | 0.21 | 50.7 | 0.39 |
| 2 | 48.5 | 0.19 | 50.6 | 0.47 |
| 3 | 48.1 | 0.22 | 50.4 | 0.47 |
| 4 | 47.6 | 0.24 | 50.4 | 0.40 |
| 5 | 47.0 | 0.26 | 49.7 | 0.41 |
| 6 | 46.5 | 0.25 | 49.9 | 0.49 |
| 7 | 45.9 | 0.29 | 49.0 | 0.67 |
| 8 | 45.3 | 0.30 | 48.9 | 0.66 |
| 9 | 44.7 | 0.33 | 48.5 | 0.69 |
| 10 | 44.0 | 0.42 | 48.0 | 0.63 |
| 11 | 43.2 | 0.42 | 47.1 | 0.65 |
| 12 | 42.6 | 0.43 | 47.1 | 0.67 |
| 13 | 42.2 | 0.44 | 47.0 | 0.69 |
| 14 | 41.4 | 0.45 | 46.8 | 0.71 |
| 15 | 40.8 | 0.51 | 46.5 | 0.77 |
| 16 | 40.2 | 0.54 | 45.9 | 0.78 |

TABLE D

| | Apertured Film | | | |
|---|---|---|---|---|
| | No | | Yes | |
| Cycle | Mean | Std | Mean | Std |
| 0 | 0.0 | 0.00 | 0.0 | 0.00 |
| 1 | −0.4 | 0.11 | −0.0 | 0.25 |
| 2 | −1.0 | 0.11 | −0.2 | 0.31 |
| 3 | −1.4 | 0.14 | −0.3 | 0.31 |
| 4 | −1.9 | 0.17 | −0.4 | 0.29 |
| 5 | −2.5 | 0.20 | −1.0 | 0.20 |
| 6 | −3.0 | 0.20 | −0.8 | 0.34 |
| 7 | −3.6 | 0.23 | −1.7 | 0.52 |
| 8 | −4.2 | 0.27 | −1.8 | 0.50 |
| 9 | −4.8 | 0.30 | −2.3 | 0.61 |
| 10 | −5.5 | 0.38 | −2.8 | 0.47 |
| 11 | −6.3 | 0.38 | −3.7 | 0.46 |
| 12 | −6.9 | 0.41 | −3.7 | 0.48 |
| 13 | −7.3 | 0.42 | −3.8 | 0.50 |
| 14 | −8.0 | 0.43 | −4.0 | 0.51 |
| 15 | −8.6 | 0.50 | −4.3 | 0.63 |
| 16 | −9.3 | 0.54 | −4.8 | 0.67 |

Soap bars without apertured film demonstrated a consistent weight loss, averaging 0.5 gram per cycle. Soap bars with apertured film lost an average of 0.3 gram per cycle, but the weight loss pattern was not strictly linear.

After the $16^{th}$ cycle was complete, soap bars without apertured film had lost a mean of 9.3 grams, versus a loss of 4.8 grams for soap bars with apertured film (P<0.001). Analysis of variance found that soap bars with apertured film had a lower cumulative weight loss than soap bars without apertured film at all 16 hand wash cycles (P<0.001). Therefore, the solid cleanser holders of the present invention make solid cleansers more efficient.

Example 2

Foam Production During Hand Washing

The foam generated during hand washing in the experiment above was weighed. The results are shown in Table G.

TABLE E

|  | Apertured Film | | | |
|---|---|---|---|---|
|  | No | | Yes | |
| Cycle | Mean | SD | Mean | SD |
| 1 | 0.70 | 0.22 | 1.82 | 0.37 |
| 2 | 0.77 | 0.13 | 1.64 | 0.18 |
| 3 | 0.90 | 0.12 | 1.81 | 0.31 |
| 4 | 0.85 | 0.15 | 1.83 | 0.37 |
| 5 | 0.89 | 0.13 | 1.84 | 0.36 |
| 6 | 0.99 | 0.23 | 2.12 | 0.39 |
| 7 | 1.03 | 0.17 | 2.09 | 0.30 |
| 8 | 1.07 | 0.14 | 1.78 | 0.29 |
| 9 | 0.97 | 0.16 | 1.84 | 0.36 |
| 10 | 1.06 | 0.15 | 1.71 | 0.27 |
| A11 | 0.92 | 0.20 | 1.85 | 0.34 |

At each of the 10 cycles and for all cycles combined, mean foam production was significantly higher when the apertured film was present (P<0.001 by analysis of variance). Inspection suggested that the foam production from bars without apertured film tended to increase as the number of cycles increased, while bars with apertured film produced a more constant level of foam. This observation was confirmed by analysis of variance: soap bars without apertured film showed a foam production mean increase of 0.037 grams per cycle (P<0.001), while the foam production from soap bars with apertured film did not change (P>0.50).

Example 3

Measurement of Slide Angle (Slip)

A test was developed to determine the slipperiness of bar soap with and without the apertured film enclosures of the invention. Ten apertured film-wrapped and unwrapped soap bars were soaked in tepid tap water (approximately 40° C.) for 10 minutes. A modified lab jack with a 20 cm×20 cm stainless steel top plate was checked for level via measuring the front height of the plate versus the end height of the plate on a level surface. A single soap bar was placed onto the stainless steel top plate and the handle was turned to alter the angle. The angle was increased until the soap bar just began to slide on the top plate. At this point, the front height and end height of the plate were again measured. The difference between these heights was the sliding height. The Angle to Slip was then calculated as:

Angle to Slip=Sin$^{-1}$ (Sliding Height/Top Plate Length)

where: top plate length=20 cm.

A higher angle to slip indicates a less slippery product. Results of this experiment are summarized in Table H:

TABLE F

|  | Mean | N | Std Dev | Std Error | Minimum | Maximum |
|---|---|---|---|---|---|---|
| No Film | 1.75° | 10 | 0.91 | 0.29 | 0.57 | 3.44 |
| Film | 5.85° | 10 | 0.72 | 0.23 | 5.16 | 7.47 |

One-way analysis of variance found that soap bars with apertured film had significantly higher slip angles than soap bars without apertured film (P<0.001). Therefore, the soap bar holders of the present invention make the soap bar less slippery.

We claim:

1. A solid cleanser holder comprising:
   a. at least one textured film having texture variations including at least one aperture; and
   b. a solid cleanser;
   wherein the at least one textured film surrounds the solid cleanser;
   wherein said textured film has an open area of no more than about 45%, based upon the total area of the textured film.

2. The solid cleanser holder of claim 1, wherein the textured film is substantially permanently sealed around the solid cleanser.

3. The solid cleanser holder of claim 1, wherein the solid cleanser is selected from the group consisting of bar, flake, pellet, chip, spray-dried powder, noodle, semi-solid, gel, moldable paste and combinations thereof.

4. The solid cleanser holder of claim 1, wherein the solid cleanser comprises soap, a synthetic surfactant, or mixtures thereof.

5. The solid cleanser holder of claim 1, wherein the solid cleanser is a soap bar.

6. The solid cleanser holder of claim 1, wherein the textured film is comprised of polyolefins, cellulosics, polyurethanes, polyamides, polyesters, metallocene polyethylenes and blends and copolymers thereof.

7. The solid cleanser holder of claim 6, wherein the textured film is comprised of polyethylenes, polypropylenes, polyvinyl acetates, polyacrylates, polyvinyl chloride, polyvinylidine chloride, polyvinyl alcohol and blends and copolymers thereof.

8. The solid cleanser holder of claim 1, wherein the aperture is in the form of a hole, slit or protuberance.

9. The solid cleanser holder of claim 1, wherein the textured film comprises multiple apertures in an amount ranging from about 0.1 apertures/cm$^2$ to about 300 apertures/cm$^2$.

10. The solid cleanser holder of claim 9, wherein the textured film comprises apertures in an amount ranging from about 1.3 apertures/cm$^2$ to about 30 apertures/cm$^2$.

11. The solid cleanser holder of claim 10, wherein the textured film comprises apertures in an amount ranging from about 1.5 apertures/cm$^2$ to about 15 apertures/cm$^2$.

12. The solid cleanser holder of claim 1, wherein the apertures have a depth of greater than 0 mm to about 3 mm.

13. The solid cleanser holder of claim 1, wherein the aperture has a diameter of about 0.01 cm to about 0.6 cm.

14. The solid cleanser holder of claim 13, wherein the diameter ranges from about 0.05 cm to 0.4 cm.

15. The solid cleanser holder of claim 14, wherein the diameter ranges from about 0.1 cm to 0.35 cm.

16. The solid cleanser holder of claim 1, wherein the texture variations comprise a combination of apertures and at least one additional texture variation selected from the group consisting of embossments, debossments, and combinations thereof.

17. The solid cleanser holder of claim 16, wherein the at least one additional texture variation is present in an amount of up to about 7000 texture variation/cm$^2$.

18. The solid cleanser holder of claim 1, wherein the at least one aperture is a protuberance facing outward away from the solid cleanser.

19. The solid cleanser holder of claim 1, wherein the at least one aperture is a protuberance facing inward toward the solid cleanser.

20. The solid cleanser holder of claim 1, comprising two different textured films, wherein the textured film comprise protuberances which are facing toward one another.

21. The solid cleanser holder of claim 1, wherein the texture variations are in the approximate shape of a circle, honeycomb, oval, heart, pear, square, triangle, polygon, stellate, rectangle, star, or combinations thereof.

22. The solid cleanser holder of claim 1, wherein the textured film has an open area of no more than about 45% based upon the total area of the textured film.

23. The solid cleanser holder of claim 22, wherein the textured film has an open area of greater than about 15% and less than about 35% based upon the total area of the textured film.

24. The solid cleanser holder of claim 1, wherein the textured film comprises a film modifier impregnated into and/or deposited onto the textured film.

25. The solid cleanser holder of claim 24, wherein the film modifier is selected from the group consisting of a surfactant, an antimicrobial agent, a colorant, a fragrance, a filler, silica, pumice, mica, and mixtures thereof.

26. The solid cleanser holder of claim 1, wherein the textured film is a coextruded layer comprising at least two layers.

27. The solid cleanser holder of claim 1, wherein the textured film comprises at least 2-plies of film sheets.

28. The solid cleanser holder of claim 27, wherein the at least 2-plies are separate substrates sealed together along the periphery.

29. The solid cleanser holder of claim 28, wherein the at least 2-plies are one substrate that is folded upon itself and then sealed.

30. The solid cleanser holder of claim 1, further comprising an inner substrate that is substantially covered by the textured film.

31. The solid cleanser holder of claim 30, wherein the inner substrate is comprised of an open-celled mesh sheet, porous foam sheet, reticulated foam sheet, natural fiber sheet, polymeric fiber sheet, spunbond fiber sheet, and combinations thereof.

32. The solid cleanser holder of claim 1, in a shape selected from the group consisting of round, oval, square, rectangle, star, polygon, hand, mitt, or animal.

33. The solid cleanser holder of claim 1 further comprising a holding means in the form of hook, loop, strap or string.

34. The solid cleanser holder of claim 33, wherein the holding means is made from a continuous piece of the textured film.

35. The solid cleanser holder of claim 1, comprising at least two textured films that are wrapped around the solid cleanser and are substantially permanently sealed together.

36. The solid cleanser holder of claim 1, comprising two different textured films, with protuberances facing toward one another, that are wrapped around the solid cleanser and sealed on three sides to substantially permanently surround the solid cleanser.

37. The solid cleanser holder of claim 1, wherein the textured film continuously surrounds the solid cleanser, wherein said textured film is gathered and secured with a securing means for substantially permanently holding the gathered textured film together.

38. The solid cleanser holder of claim 1, wherein the textured film continuously surrounds the solid cleanser and is sealed on at least one side.

39. The solid cleanser holder of claim 1, having an angle to slip of at least 5°.

40. A method of reducing solid cleanser slip comprising enclosing the solid cleanser within a textured film such that the textured film surrounds the solid cleanser, wherein the textured film comprises texture variations including at least one aperture and wherein said textured film has an open area of no more than about 45%, based upon the total area of the textured film.

41. A method of improving the lathering abilities of a solid cleanser comprised of enclosing the solid cleanser within a textured film such that the textured film surrounds the solid cleanser, wherein the textured film comprises texture variations including at least one aperture and wherein said textured film has an open area of no more than about 45%, based upon the total area of the textured film.

42. A method of ameliorating the formation of mush on a solid cleanser comprised of enclosing the solid cleanser within a textured film such that the textured film surrounds the solid cleanser, wherein said textured film comprises texture variations including at least one aperture and wherein said textured film has an open area of no more than about 45%, based upon the total area of the textured film.

43. A method of reducing the wear rate of a solid cleanser comprised of enclosing the solid cleanser within a textured film such that the textured film surrounds the solid cleanser, wherein the textured film comprises texture variations including at least one aperture and wherein said textured film has an open area of no more than about 45%, based upon the total area of the textured film.

44. A method of cleaning the skin comprised of wetting the solid cleanser holder of claim 1 with water;
applying agitation to the wet solid cleanser holder, wherein the amount of water and agitation is sufficient to create a lather on the solid cleanser holder, applying said lathering solid cleanser holder to the skin, and rinsing with water.

45. A method of exfoliating the skin comprised of wetting the solid cleanser holder of claim 1 with water;
applying agitation to the wet solid cleanser holder, wherein the amount of water and agitation is sufficient to create a lather on the solid cleanser holder, applying said lathering solid cleanser holder to the skin, and rinsing with water.

46. A method of making a solid cleanser holder said method comprised of enclosing a solid cleanser within a textured film such that the textured film surrounds the solid cleanser, wherein the textured film comprises texture variations including at least one aperture and wherein said textured film has an open area of no more than about 45%, based upon the total area of the textured film.

47. The method of claim 46, wherein the textured film is substantially permanently sealed around the solid cleanser.

48. The method of claim 47, wherein the textured film is substantially permanently sealed around the solid cleanser using a sealing process selected from the group consisting of heat seal, heat shrink, ultrasonic seal, adhesive seal, stitch seal, and pressure seal.

49. The method of claim 46, wherein the textured film is sealed on at least two sides.

* * * * *